(12) United States Patent
Kontani (10) Patent No.: US 9,470,631 B2
(45) Date of Patent: Oct. 18, 2016

(54) SPR SENSOR CELL AND SPR SENSOR (71) Applicant: NITTO DENKO CORPORATION, Osaka (JP)

(72) Inventor: Tomohiro Kontani, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 14/401,824

(22) PCT Filed: May 16, 2013

(86) PCT No.: PCT/JP2013/063640
§ 371 (c)(1),
(2) Date: Nov. 17, 2014

(87) PCT Pub. No.: WO2013/179900
PCT Pub. Date: Dec. 5, 2013

(65) Prior Publication Data
US 2015/0147021 A1    May 28, 2015

(30) Foreign Application Priority Data
Jun. 1, 2012 (JP) .................................. 2012-125854

(51) Int. Cl.
G02B 6/00 (2006.01)
G01N 21/552 (2014.01)
G01N 21/17 (2006.01)
G02B 6/10 (2006.01)

(52) U.S. Cl.
CPC ............ G01N 21/553 (2013.01); G01N 21/17 (2013.01); G02B 6/10 (2013.01)

(58) Field of Classification Search
None
See application file for complete search history.

(56) References Cited

U.S. PATENT DOCUMENTS

| | | |
|---|---|---|
| 6,432,364 B1 | 8/2002 | Negami et al. |
| 7,046,362 B2 | 5/2006 | Lehmann et al. |
| 7,318,909 B2 | 1/2008 | Lehmann et al. |
| 7,352,468 B2 | 4/2008 | Tarsa |
| 7,504,068 B2 | 3/2009 | Lehmann et al. |
| 7,504,263 B2 | 3/2009 | Lehmann et al. |
| 8,072,606 B2 * | 12/2011 | Chau .................... G01N 21/554 356/445 |
| 8,355,134 B2 * | 1/2013 | Chau .................... B82Y 20/00 356/445 |

(Continued)

FOREIGN PATENT DOCUMENTS

| CN | 101128730 A | 2/2008 |
|---|---|---|
| CN | 102128809 A | 7/2011 |

(Continued)

OTHER PUBLICATIONS

ISA Japanese Patent Office, International Search Report of PCT/JP2013/063640, Jun. 18, 2013, WIPO, 3 pages.

(Continued)

*Primary Examiner* — Rhonda Peace
(74) *Attorney, Agent, or Firm* — Alleman Hall McCoy Russell & Tuttle LLP (57) ABSTRACT

There are provided an SPR sensor cell and an SPR sensor having a very excellent detection sensitivity. The SPR sensor cell of the present invention includes: an under-cladding layer; a core layer formed so that at least a part of the core layer is adjacent to the under-cladding layer and having a light entrance and a light exit; and a metal layer covering a part of the core layer. A sectional area (S1) of the core layer at the light entrance and a sectional area (S2) of the core layer at the part covered by the metal layer satisfy a relationship of S1>S2.

5 Claims, 7 Drawing Sheets

(56) References Cited

U.S. PATENT DOCUMENTS

| | | | | |
|---|---|---|---|---|
| 8,718,420 B2* | 5/2014 | Kontani | ............... | G01N 21/553 385/12 |
| 9,012,830 B2* | 4/2015 | Zhu | ................... | G01N 21/7746 250/227.14 |
| 9,075,009 B2* | 7/2015 | Kim | ...................... | G01N 21/552 |
| 9,285,534 B2* | 3/2016 | Lee | ........................... | G02B 6/02 |
| 2003/0107739 A1 | 6/2003 | Lehmann et al. | | |
| 2003/0109055 A1 | 6/2003 | Lehmann et al. | | |
| 2004/0118997 A1 | 6/2004 | Lehmann et al. | | |
| 2005/0117157 A1 | 6/2005 | Tarsa | | |
| 2006/0177939 A1 | 8/2006 | Lehmann et al. | | |
| 2006/0183241 A1 | 8/2006 | Lehmann et al. | | |
| 2009/0066962 A1* | 3/2009 | Niwa | .................. | G01N 21/553 356/445 |
| 2009/0136190 A1* | 5/2009 | Berini | .................... | B82Y 20/00 385/130 |
| 2010/0182607 A1* | 7/2010 | Chau | .................... | G01N 21/554 356/445 |
| 2013/0077912 A1* | 3/2013 | Kontani | ............... | G01N 21/553 385/12 |
| 2013/0259418 A1* | 10/2013 | Kontani | ............... | G01N 21/553 385/12 |
| 2014/0017125 A1* | 1/2014 | Kontani | .................. | G01N 21/03 422/69 |
| 2014/0017126 A1* | 1/2014 | Kontani | .................. | G01N 21/03 422/69 |
| 2014/0132959 A1* | 5/2014 | Kontani | ............... | G01N 21/553 356/445 |
| 2014/0363336 A1* | 12/2014 | Kontani | ............... | G01N 21/553 422/69 |
| 2015/0029502 A1* | 1/2015 | Kontani | ............... | G01N 21/553 356/246 |
| 2015/0042998 A1* | 2/2015 | Kontani | ............... | G01N 21/553 356/445 |
| 2015/0147021 A1* | 5/2015 | Kontani | ............... | G01N 21/553 385/12 |
| 2015/0260649 A1* | 9/2015 | Nishio | ................. | G01N 21/553 385/12 |

FOREIGN PATENT DOCUMENTS

| | | |
|---|---|---|
| CN | 102262073 A | 11/2011 |
| JP | 200019100 A | 1/2000 |
| JP | 2008525802 A | 7/2008 |
| JP | 2010223610 A | 10/2010 |
| JP | 2010223817 A | 10/2010 |
| JP | 2012021973 A | 2/2012 |
| WO | 9715820 A1 | 5/1997 |

OTHER PUBLICATIONS

Verma, R. et al., "Modeling of Tapered Fiber-Optic Surface Plasmon Resonance Sensor With Enhanced Sensitivity," IEEE Photonics Technology Letters, vol. 19, No. 22, Nov. 15, 2007, 3 pages.

Boiragi, I. et al., "Evanescent Field Absorption Based Photonic Polymer Waveguide Biosensor," Photonics 2010: Tenth International Conference on Fiber Optics and Photonics, SPIE 8173, Jul. 22, 2011, 7 pages.

European Patent Office, Extended European Search Report Issued in Application No. 13796595.0, Dec. 16, 2015, Germany, 8 pages.

State Intellectual Property Office of the People's Republic of China, First Office Action Issued in Chinese Patent Application No. 201380025926.X, Dec. 21, 2015, 12 pages.

* cited by examiner

SPR SENSOR CELL AND SPR SENSOR

TECHNICAL FIELD

The present invention relates to an SPR sensor cell and an SPR sensor. More specifically, the present invention relates to an SPR sensor cell including an optical waveguide and an SPR sensor.

BACKGROUND ART

Hitherto, in the fields of chemical analysis, biochemical analysis, and the like, a surface plasmon resonance (SPR) sensor including an optical fiber has been used. In the SPR sensor including an optical fiber, a metal thin film is formed on an outer circumferential surface of a tip end portion of the optical fiber, and an analysis sample is fixed to the optical fiber into which light is guided. Among the light to be guided, light having a particular wavelength generates surface plasmon resonance in the metal thin film, and light intensity thereof is attenuated. In such an SPR sensor, the wavelength of the light generating surface plasmon resonance generally varies depending on a refractive index or the like of an analysis sample to be fixed to the optical fiber. Therefore, if a wavelength at which light intensity is attenuated after the generation of surface plasmon resonance is measured, the wavelength of the light generating surface plasmon resonance can be identified. Further, if a change in the wavelength at which light intensity is attenuated is detected, it can be confirmed that the wavelength of the light generating surface plasmon resonance has changed, and hence a change in refractive index of the analysis sample can be confirmed. As a result, such an SPR sensor can be used for various chemical analyses and biochemical analyses such as measurement of a sample concentration and detection of an immunoreaction.

For example, in the case where the sample is a solution, the refractive index of the sample (solution) depends on a concentration of the solution. Therefore, the concentration of the sample can be detected by measuring the refractive index of the sample (solution) in the SPR sensor in which the sample (solution) is in contact with the metal thin film, and further, it can be confirmed that the concentration of the sample (solution) has changed by confirming a change in the refractive index. In an analysis of the immunoreaction, for example, an antibody is fixed onto the metal thin film of the optical fiber in the SPR sensor through intermediation of a dielectric film, an analyte is brought into contact with the antibody, and surface plasmon resonance is generated. In this case, if the antibody and the analyte perform the immunoreaction, the refractive index of the sample changes. Therefore, it can be determined that the antibody and the analyte have performed the immunoreaction by confirming that the refractive index of the sample has changed before and after contact between the antibody and the analyte.

In the SPR sensor including an optical fiber, the tip end portion of the optical fiber has a fine cylindrical shape, and hence there is a problem in that it is difficult to form the metal thin film and fix an analysis sample to the optical fiber. In order to solve the problem, for example, there has been proposed an SPR sensor cell including a core through which light is transmitted and a clad covering the core, in which a through-hole extending to a surface of the core is formed at a predetermined position of the clad, and a metal thin film is formed on the surface of the core at a position corresponding to the through-hole (for example, Patent Literature 1). In such an SPR sensor cell, it is easy to form the metal thin film for generating surface plasmon resonance on the surface of the core and fix the analysis sample onto the surface.

However, in recent years, in chemical analysis and biochemical analysis, there is an increasing demand for detection of a minute change and/or a trace amount of component, and thus further enhancement of detection sensitivity of the SPR sensor cell is being demanded.

CITATION LIST

Patent Literature

[PTL 1] JP 2000-19100 A

SUMMARY OF INVENTION

Technical Problem

The present invention has been made in view of solving the conventional problem, and an object of the present invention is to provide an SPR sensor cell and an SPR sensor, each having a very excellent detection sensitivity.

Solution to Problem

According to one embodiment of the present invention, there is provided an SPR sensor cell. The SPR sensor cell includes: an under-cladding layer; a core layer formed so that at least a part of the core layer is adjacent to the under-cladding layer and having a light entrance and a light exit; and a metal layer covering a part of the core layer. A sectional area (S1) of the core layer at the light entrance and a sectional area (S2) of the core layer at the part covered by the metal layer satisfy a relationship of S1>S2.

In one embodiment of the present invention, the sectional area (S1) of the core layer at the light entrance and the sectional area (S2) of the core layer at the part covered by the metal layer satisfy a relationship of S1×0.5≥S2.

In one embodiment of the present invention, a thickness of the core layer at the part covered by the metal layer is 25 μm or less.

In one embodiment of the present invention, a thickness of the core layer at the light entrance is 50 μm or more.

In one embodiment of the present invention, a width of the core layer at the light entrance is 50 μm or more.

According to another aspect of the present invention, an SPR sensor is provided. The SPR sensor includes the SPR sensor cell as described above.

Advantageous Effects of Invention

According to an embodiment of the present invention, the SPR sensor cell and the SPR sensor, both having an extremely excellent detection sensitivity, can be provided by changing the shape of the core layer in an optical waveguide functioning as a detection unit to promote SPR excitation.

BRIEF DESCRIPTION OF DRAWINGS

FIG. 3(b)

is a schematic sectional view of the SPR sensor cell, illustrated in FIG. 1, taken along the line Ib-Ib.

DESCRIPTION OF EMBODIMENTS

A. SPR Sensor Cell

Figure 1:
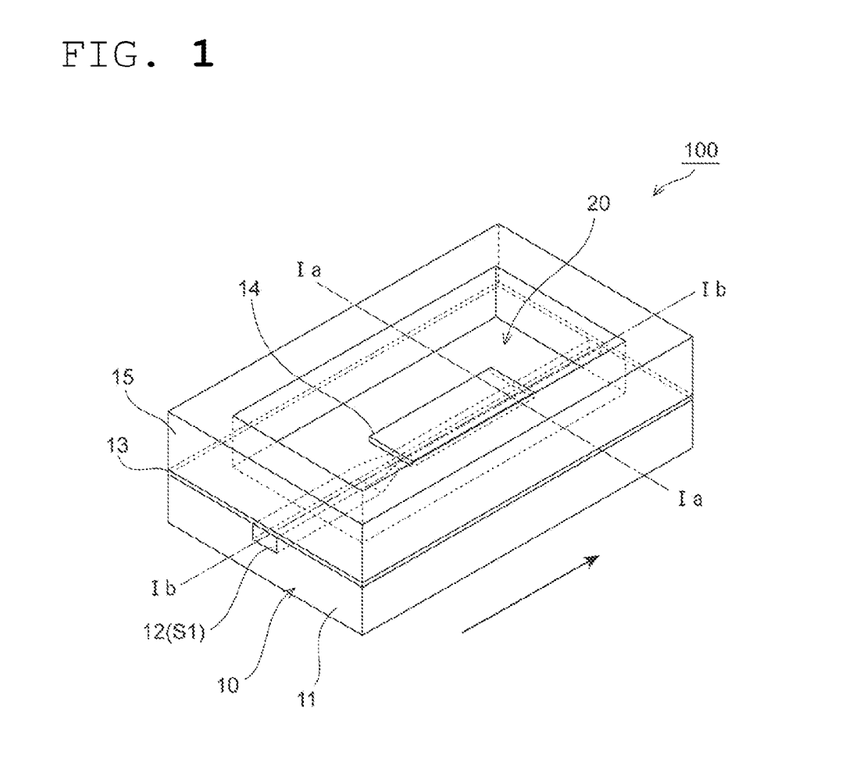
FIG. 1 is a schematic perspective view illustrating an SPR sensor cell according to a preferred embodiment of the present invention.
Figure 2:
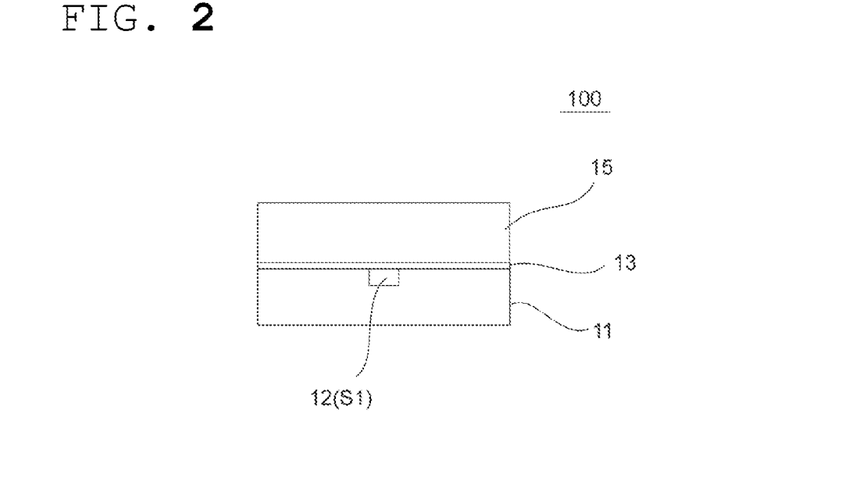
FIG. 2 is a schematic lateral view of the SPR sensor cell illustrated in FIG. 1 as viewed from a light entrance side.
Figure 3A:
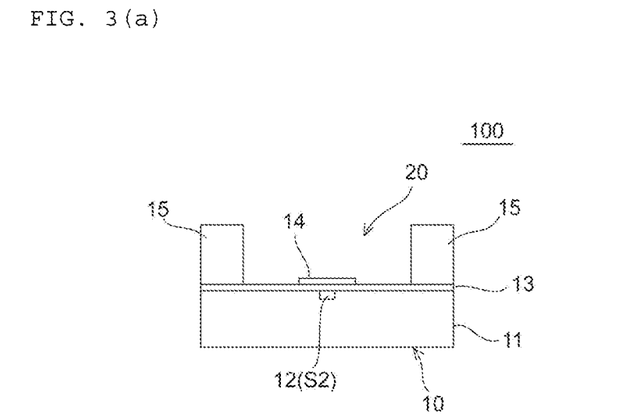
FIG. 3(a) is a schematic sectional view of the SPR sensor cell illustrated in FIG. 1 taken along the line Ia-Ia.
Figure 3B:
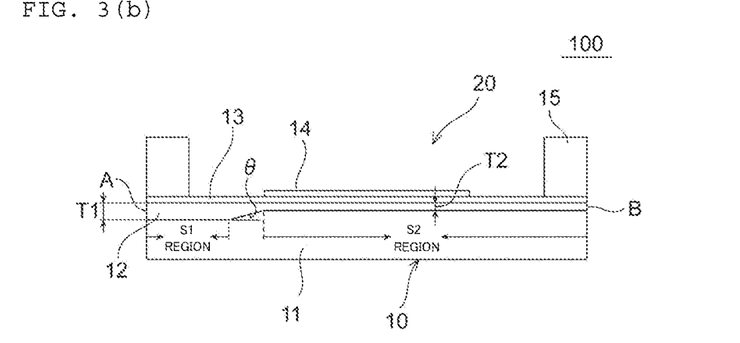
Figure 3C:
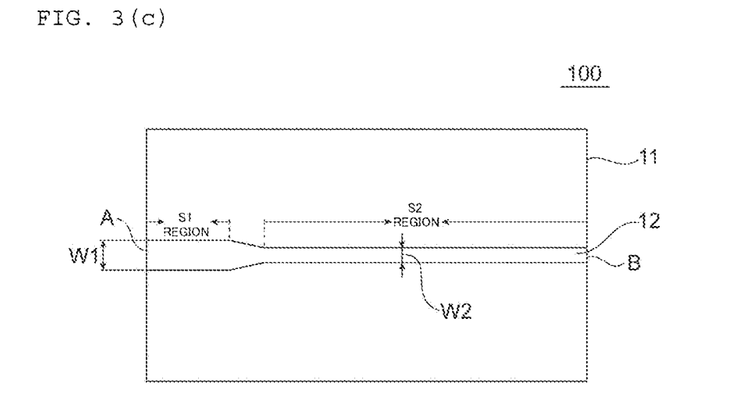
FIG. 3(c) is a schematic horizontal sectional view of the SPR sensor cell, illustrated in FIG. 1, cut along a plane passing through a core layer of the SPR sensor cell.

FIG. 1 is a schematic perspective view illustrating an SPR sensor cell according to a preferred embodiment of the present invention. In the SPR sensor cell, light enters and travels in the direction indicated by the arrow. FIG. 2 is a schematic lateral view of the SPR sensor cell illustrated in FIG. 1 as viewed from a light entrance side. FIGS. 3(a), 3(b), and 3(c) are a schematic sectional view of the SPR sensor cell illustrated in FIG. 1 taken along the line Ia-Ia, a schematic sectional view of the SPR sensor cell taken along the line Ib-Ib, and a schematic horizontal sectional view of the SPR sensor cell cut along a plane passing through a core layer of the SPR sensor cell, respectively. In the below-indicated description of the SPR sensor cell, when a direction is mentioned, the upper side of the drawing sheet is defined as an upper side, and the lower side of the drawing sheet is defined as a lower side.

An SPR sensor cell 100 includes: an under-cladding layer 11; a core layer 12 formed so that at least a part thereof is adjacent to the under-cladding layer 11 and having a light entrance A and a light exit B; a protective layer 13 covering the upper surface of each of the under-cladding layer 11 and the core layer 12; and a metal layer 14 formed on the protective layer 13 and covering a part of the core layer 12. In the illustrated embodiment, the under-cladding layer 11, the core layer 12, the protective layer 13, and the metal layer 14 constitute an optical waveguide and function as a detection unit 10 for detecting the state of a sample and/or a change therein. In a practical case, the SPR sensor cell 100 includes a sample mounting portion 20 formed so as to be adjacent to the detection unit 10. The sample mounting portion 20 is defined by an over-cladding layer 15. The protective layer 13 may be omitted depending on the purpose. The over-cladding layer 15 may also be omitted as long as the sample mounting portion 20 can be provided appropriately. In the sample mounting portion 20, a sample (for example, a solution or powder) to be analyzed is mounted so as to come into contact with the detection unit (substantially, the metal layer).

The under-cladding layer 11 is formed in a shape of a plate having a substantially rectangular shape in a plan view, with a predetermined thickness. The thickness of the under-cladding layer (thickness from an upper surface of the core layer) is, for example, from 50 μm to 900 μm.

The core layer 12 is formed so as to extend in a direction perpendicular to both a width direction (right and left direction of the figure surface of FIG. 2 and a thickness direction of the under-cladding layer 11, and is buried in an upper end portion substantially at the center of the width direction of the under-cladding layer 11. The direction in which the core layer 12 extends serves as a direction in which light is propagated in the optical waveguide.

The core layer 12 is disposed so that the upper surface thereof is exposed from the under-cladding layer 11. Preferably, the core layer 12 is disposed so that the upper surface thereof is flush with an upper surface of the under-cladding layer 11. The metal layer 14 can be disposed efficiently only on an upper side of the core layer 12 by disposing the core layer so that the upper surface thereof is flush with the upper surface of the under-cladding layer. Further, the core layer 12 is disposed so that both end surfaces thereof in the extending direction are flush with both end surfaces of the under-cladding layer in the extending direction.

In the present invention, a sectional area (S1) of the core layer 12 at the light entrance A and a sectional area (S2) of the core layer 12 at the part covered by the metal layer 14 satisfy the relationship of S1>S2, and preferably satisfy the relationship of S1×0.5≧S2. When such a relationship is satisfied, light that has entered through the light entrance can be condensed in the vicinity of the metal layer 14. As a result, SPR excitation is promoted, and hence excellent detection sensitivity can be obtained. It should be noted that, when the sectional shape at the part covered by the metal layer is not constant (for example, when the thickness and/or the width varies), the minimum value of the sectional area in the part is defined as S2, and it suffices that the minimum value (S2) be smaller than S1.

The shape of the core layer 12 may be any appropriate shape as long as the relationship of S1>S2 is satisfied. For example, the core layer 12 is formed so as to: have a region (S1 region) including the light entrance and having the sectional area S1, and a substantially column-shaped region (S2 region) including at least a part, preferably the entirety of the part covered by the metal layer 14 and having the sectional area S2; and have a sectional area that gradually decreases toward the S2 region between the S1 region and the S2 region. The S2 region is preferably formed so as to include the light exit. When the S2 region does not include the light exit, a region ranging from the end portion of the S2 region on the light exit side to the light exit may be formed so that the sectional area of the light exit is larger than S2.

In an embodiment illustrated in FIGS. 3(a) to 3(c), in the core layer 12, a region ranging from the light entrance A to a predetermined portion serves as the S1 region having a substantially square column shape, a region ranging from the end portion of the S1 region on the light exit side to the end portion of the part covered by the metal layer 14 on the light entrance side is formed so as to have a tapered shape as a shape in a plan view with a sloped thickness that gradually decreases, and a region ranging from the end portion of the part covered by the metal layer 14 on the light entrance side to the light exit B serves as the S2 region having a substantially square column shape.

In the region between the S1 region and the S2 region, both the thickness and the width may be changed, or only one thereof (for example, only the thickness) may be changed. When the thickness is changed, an inclination angle θ is preferably 5° or less, more preferably 3° or less, still more preferably 1° or less. With such an inclination angle, the loss of light that has entered through the light entrance can be suitably suppressed.

A thickness of the core layer 12 at the part covered by the metal layer 14 (the thickness of a part having the minimum sectional area in the case where the sectional shape of the part is not constant: T2) is preferably smaller than a thickness (T1) of the core layer 12 at the light entrance. The lower limit value of the thickness (T1) of the core layer 12 at the light entrance is preferably 50 μm or more, more preferably 100 μm or more, and the upper limit value is, for example, 500 μm or less. The upper limit value of the thickness (T2) of the core layer 12 at the part covered by the metal layer 14 is, for example, 50 μm or less, preferably less than 50 μm, more preferably 25 μm or less, still more preferably 15 μm or less, particularly preferably 5 μm or less, and the lower limit value is, for example, 2 μm or more. In one embodiment, T2/T1 may be preferably ½ or less, more preferably ¼ or less, still more preferably ⅕ or less. When the thickness of the core layer 12 is adjusted as just described, light that has entered through the light entrance can be efficiently condensed in the vicinity of the metal layer 14.

A width of the core layer 12 at the part covered by the metal layer 14 (the width of a part having the minimum sectional area in the case where the sectional shape of the part is not constant: W2) is preferably equal to or smaller than a width (W1) of the core layer 12 at the light entrance. The lower limit value of the width (W1) of the core layer 12 at the light entrance is preferably 50 μm or more, more preferably 100 μm or more, and the upper limit value is, for example, 500 μm or less. In addition, the upper limit value of the width (W2) of the core layer 12 at the part covered by the metal layer 14 is preferably 50 μm or less, more preferably 25 μm or less, still more preferably 15 μm or less, particularly preferably 5 μm or less, and the lower limit value is, for example, 2 μm or more. When the width of the core layer 12 is adjusted as just described, light that has entered through the light entrance can be efficiently condensed in the vicinity of the metal layer 14.

The thickness and width of the core layer 12 at the light exit may be equal to or larger than the thickness and width of the core layer 12 at the part covered by the metal layer 14, respectively, and may be preferably equal to the thickness and width at the part covered by the metal layer.

The refractive index of the core layer 12 is preferably from 1.33 to 1.59. With such a refractive index, SPR excitation can be caused even in an aqueous solution-based sample (refractive index of water: 1.33) and excellent detection sensitivity can be obtained for a general-purpose material sample. It should be noted that the term "refractive index" as used herein refers to a refractive index at a wavelength of 850 nm unless otherwise specified.

The refractive index of the core layer 12 is higher than that of the under-cladding layer 11. The difference between the refractive index of the core layer and that of the under-cladding layer is preferably 0.010 or more, and more preferably 0.020 or more. When the difference between the refractive index of the core layer and that of the under-cladding layer falls within such range, the optical waveguide of the detection unit can be set to a so-called multimode. Thus, the amount of light transmitted through the optical waveguide can be increased, and as a result, the S/N ratio can be enhanced.

As a material for forming the core layer 12, any suitable material can be used as long as the effects of the present invention can be obtained. Specific examples thereof include a fluorine resin, an epoxy resin, a polyimide resin, a polyamide resin, a silicone resin, an acrylic resin, and modified products thereof (for example, a fluorene-modified product, a deuterium-modified product, and a fluorine-modified product in the case of resins other than fluorine resin). These resins may be used alone or in combination. These resins can each be used as a photosensitive material preferably by being blended with a photosensitizing agent. The under-cladding layer 11 can be formed of a material that is similar to that for forming the core layer and is adjusted so that the refractive index thereof becomes lower than that of the core layer.

As required, the protective layer 13 may be formed as a thin film having the same shape as that of the under-cladding layer in a plan view so as to cover the entire upper surface of each of the under-cladding layer 11 and the core layer 12. The formation of the protective layer 13 can, for example, prevent the core layer and/or the cladding layer from swelling with a sample when the sample is liquid. A material for forming the protective layer 13 is, for example, silicon dioxide or aluminum oxide. Such material may be preferably adjusted so as to have a lower refractive index than that of the core layer 12. The protective layer 13 has a thickness of preferably from 1 nm to 100 nm, and more preferably from 5 nm to 20 nm.

As illustrated in FIG. 1, the metal layer 14 is formed so as to uniformly cover a part of the upper surface of the core layer 12 through intermediation of the protective layer 13. In this case, as necessary, an easy-adhesion layer (not shown) may be formed between the protective layer 13 and the metal layer 14. By forming the easy-adhesion layer, the protective layer 13 and the metal layer 14 can be firmly fixed to each other. The core layer 12 may be directly covered by the metal layer 14 without the formation of the protective layer 13.

As a material for forming the metal layer 14, there may be given gold, silver, platinum, copper, aluminum, and alloys thereof. The metal layer 14 may be a single layer or may have a laminate structure of two or more layers. The thickness (total thickness of all the layers in the case of the laminate structure) of the metal layer 14 is preferably from 40 nm to 70 nm, and more preferably from 50 nm to 60 nm.

As a material for forming the easy-adhesion layer, there may be typically given chromium or titanium. The thickness of the easy-adhesion layer is preferably from 1 nm to 5 nm.

As illustrated in FIG. 1, the over-cladding layer 15 is formed in the shape of a frame having a rectangular shape in a plan view so that an outer circumference of the over-cladding layer 15 becomes substantially flush with an outer circumference of the under-cladding layer 11 in a plan view, on the upper surface of each of the under-cladding layer 11 and the core layer 12 (upper surface of the protective layer 13 in the illustrated example). A portion surrounded by the upper surfaces of the under-cladding layer 11 and the core layer 12 (upper surface of the protective layer 13 in the illustrated example) and the over-cladding layer 15 is partitioned as the sample mounting portion 20. By mounting a sample in the partitioned portion, the metal layer of the detection unit 10 and the sample come into contact with each other so that detection can be performed. Further, by forming such partitioned portion, a sample can be easily mounted on the surface of the metal layer, and hence the operability can be enhanced.

As a material for forming the over-cladding layer 15, for example, there may be given the materials for forming the core layer and the under-cladding layer, and silicone rubber. The thickness of the over-cladding layer is preferably from 5 µm to 2,000 µm, and more preferably from 25 µm to 200 µm. The refractive index of the over-cladding layer is preferably lower than the refractive index of the core layer. In one embodiment, the refractive index of the over-cladding layer is equal to the refractive index of the under-cladding layer. It should be noted that, when a protective layer having a lower refractive index than that of the core layer is formed, the refractive index of the over-cladding layer does not need to be lower than the refractive index of the core layer.

While the SPR sensor cell according to the preferred embodiment of the present invention has been described, the present invention is not limited thereto. For example, referring to FIGS. 4(*a*) to 4(*c*), 5(*a*) to 5(*c*), and 6(*a*) to 6(*c*), modifications of the SPR sensor cell illustrated in FIG. 1 can be described. SPR sensor cells illustrated in FIGS. 4(*a*) to 4(*c*), 5(*a*) to 5(*c*), and 6(*a*) to 6(*c*) each have basically the same construction as the construction of the SPR sensor cell illustrated in FIG. 1 and differ only in the shape of the core layer 12 (and the shape of the under-cladding layer corresponding to the shape of the core layer 12). Specifically, the SPR sensor cells illustrated in FIGS. 4(*a*) to 4(*c*), 5(*a*) to 5(*c*), and 6(*a*) to 6(*c*) are as described below.

Figure 4A:
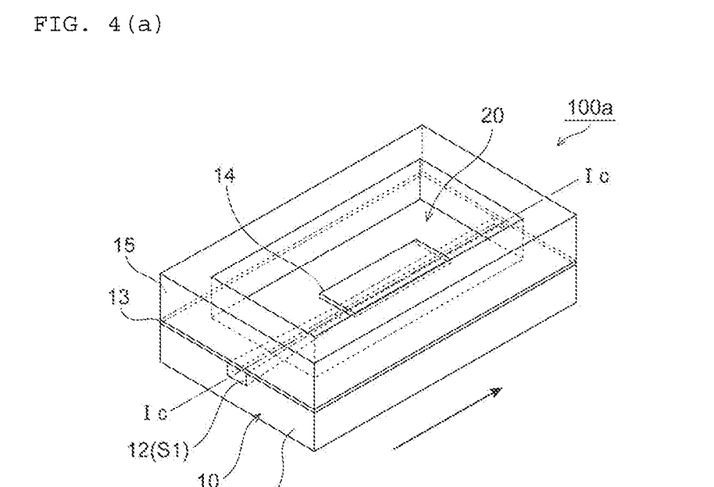
FIGS. 4(a), 4(b), and 4(c) are a schematic perspective view of an SPR sensor cell of a first modification, a schematic sectional view of the SPR sensor cell of the modification taken along the line Ic-Ic, and a schematic horizontal sectional view of the SPR sensor cell of the modification cut along a plane passing through the core layer, respectively.
Figure 4B:
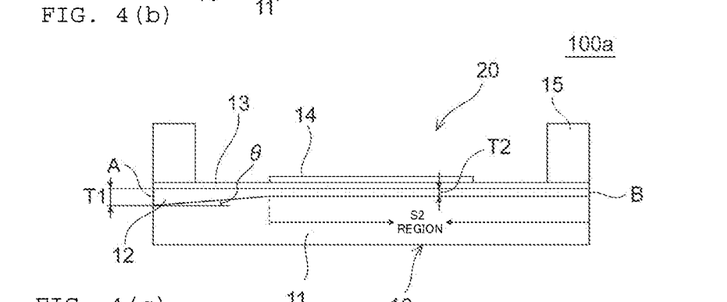
Figure 4C:
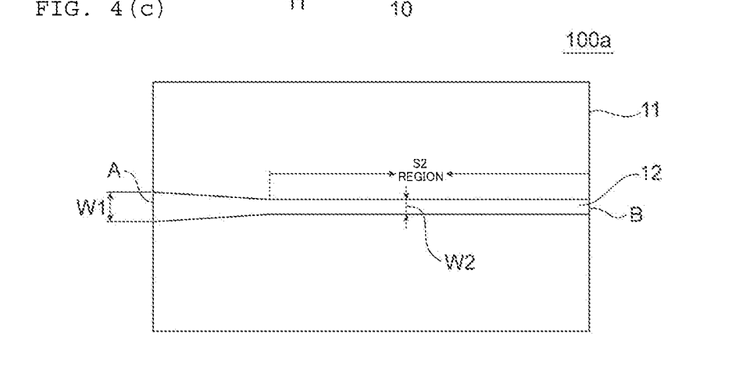

FIGS. 4(*a*), 4(*b*), and 4(*c*) are a schematic perspective view of an SPR sensor cell of a first modification, a schematic sectional view of the SPR sensor cell of the modification taken along the line Ic-Ic, and a schematic horizontal sectional view of the SPR sensor cell of the modification cut along a plane passing through the core layer, respectively. In the core layer 12 of an SPR sensor cell 100*a* of the first modification, a region (S1 region) ranging from the light entrance A to the end portion of the part covered by the metal layer 14 on the light entrance side is formed so as to have a tapered shape as a shape in a plan view with a sloped thickness that gradually decreases, and a region ranging from the end portion of the part covered by the metal layer 14 on the light entrance side to the light exit B serves as the S2 region having a substantially square column shape.

Figure 5A:
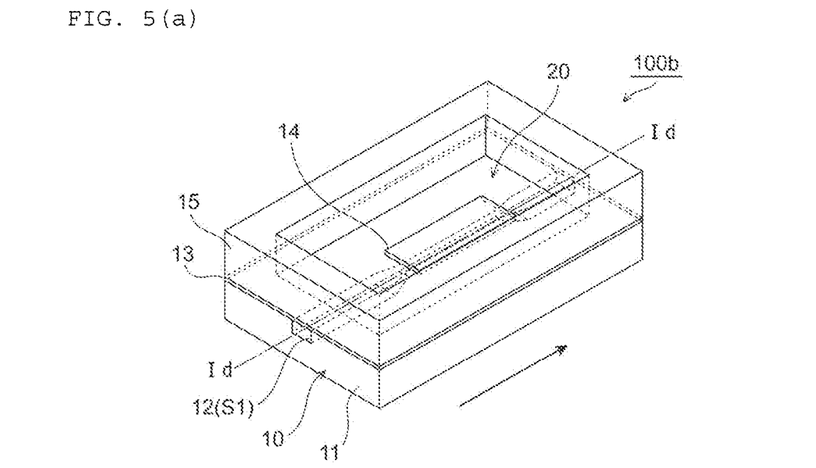
FIGS. 5(a), 5(b), and 5(c) are a schematic perspective view of an SPR sensor cell of a second modification, a schematic sectional view of the SPR sensor cell of the modification taken along the line Id-Id, and a schematic horizontal sectional view of the SPR sensor cell of the modification cut along a plane passing through the core layer, respectively.
Figure 5B:
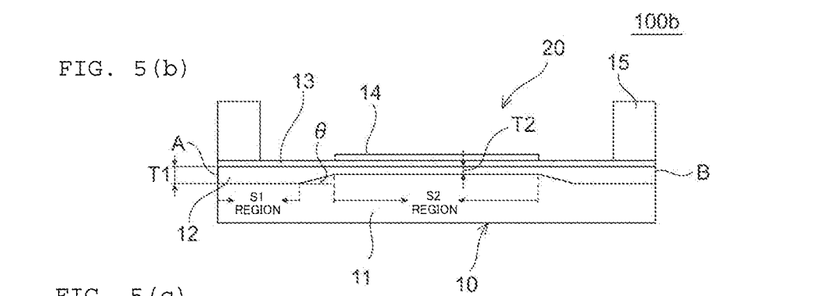
Figure 5C:
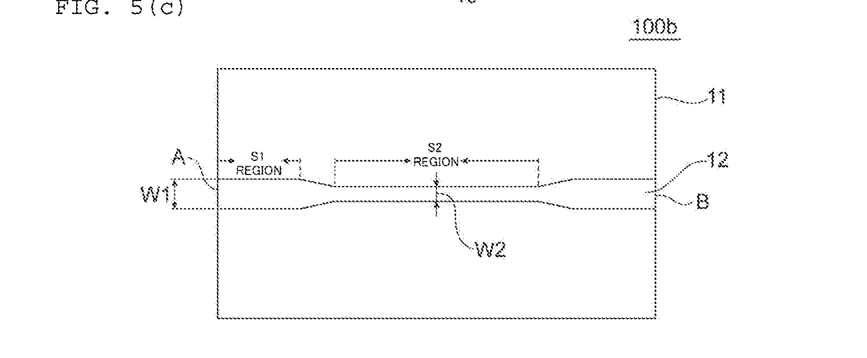

FIGS. 5(*a*), 5(*b*), and 5(*c*) are a schematic perspective view of an SPR sensor cell of a second modification, a schematic sectional view of the SPR sensor cell of the modification taken along the line Id-Id, and a schematic horizontal sectional view of the SPR sensor cell of the modification cut along a plane passing through the core layer, respectively. In the core layer 12 of an SPR sensor cell 100*b* of the second modification, a region ranging from the light entrance A to a predetermined portion serves as the S1 region having a substantially square column shape, a region ranging from the end portion of the S1 region on the light exit side to the end portion of the part covered by the metal layer 14 on the light entrance side is formed so as to have a tapered shape as a shape in a plan view with a sloped thickness that gradually decreases, the entirety of the part covered by the metal layer 14 serves as the S2 region having a substantially square column shape, a region ranging from the end portion of the S2 region on the light exit side to a predetermined portion is formed so as to have a reverse tapered shape as a shape in a plan view with a sloped thickness that gradually increases, and a region ranging from the end portion of the region on the light exit side to the light exit B is formed in a substantially square column shape having the sectional area S1.

Figure 6A:
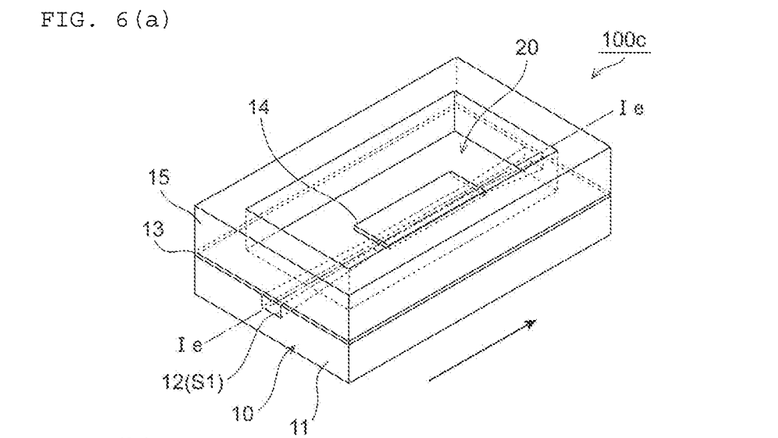
FIGS. 6(a), 6(b), and 6(c) are a schematic perspective view of an SPR sensor cell of a third modification, a schematic sectional view of the SPR sensor cell of the modification taken along the line Ie-Ie, and a schematic horizontal sectional view of the SPR sensor cell of the modification cut along a plane passing through the core layer, respectively.
Figure 6B:
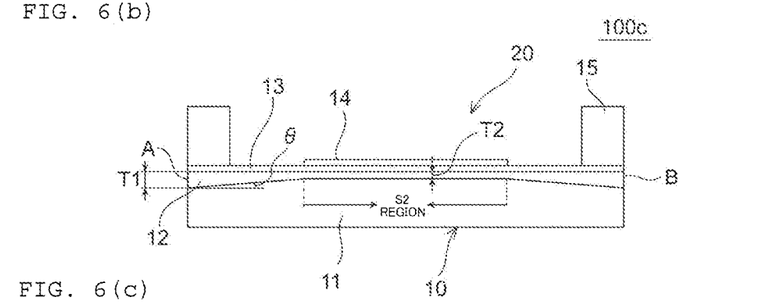
Figure 6C:
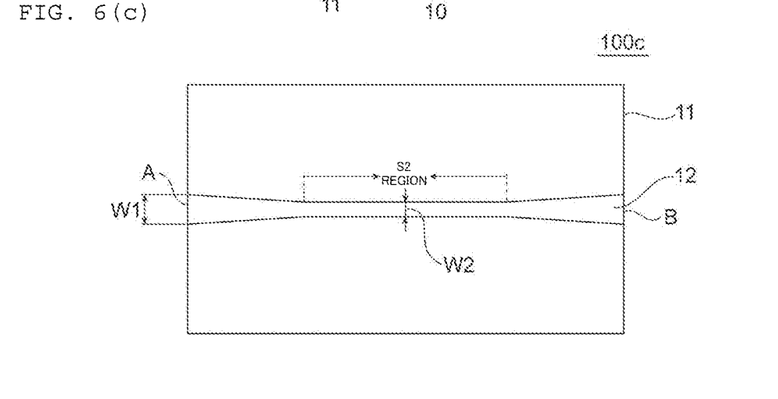

FIGS. 6(*a*), 6(*b*), and 6(*c*) are a schematic perspective view of an SPR sensor cell of a third modification, a schematic sectional view of the SPR sensor cell of the modification taken along the line Ie-Ie, and a schematic horizontal sectional view of the SPR sensor cell of the modification cut along a plane passing through the core layer, respectively. In the core layer 12 of a SPR sensor cell 100*c* of the third modification, a region (S1 region) ranging from the light entrance A to the end portion of the part covered by the metal layer 14 on the light entrance side is formed so as to have a tapered shape as a shape in a plan view with a sloped thickness that gradually decreases, the entirety of the part covered by the metal layer 14 serves as the S2 region having a substantially square column shape, and a region ranging from the end portion of the S2 region on the light exit side to the light exit B is formed so as to have a reverse tapered shape as a shape in a plan view with a sloped thickness that gradually increases.

In addition, the present invention is not limited to the embodiments described above, and for example, in the relationship between the core layer and the under-cladding layer, the layers only need to be formed so that at least a part of the core layer is adjacent to the under-cladding layer. For example, in the above-mentioned embodiments, the construction in which the core layer is buried in the under-cladding layer has been described. However, the core layer may be formed so as to penetrate through the under-cladding layer. In addition, there may be adopted a construction in which the core layer is formed on the under-cladding layer and a predetermined part of the core layer is surrounded by the over-cladding layer.

Further, the number of core layers in the SPR sensor may be changed depending on the purpose. Specifically, a plurality of the core layers may be formed at a predetermined interval in the width direction of the under-cladding layer. With such construction, a plurality of samples can be analyzed simultaneously, and hence analysis efficiency can be enhanced. As the shape of the core layer, any suitable shape (for example, a semicircular shape or a convex shape as a sectional shape) can be adopted depending on the purpose.

Further, a lid may be provided on an upper portion of the SPR sensor cell 100 (sample mounting portion 20). With such construction, a sample can be prevented from coming into contact with ambient air. In addition, in the case where the sample is a solution, a change in concentration caused by evaporation of a solvent can be prevented. In the case of providing a lid, an injection port for injecting a liquid sample into the sample mounting portion and a discharge port for discharging the liquid sample from the sample mounting portion may be provided. With such construction, the sample can be allowed to flow and supply the sample mounting portion continuously, and hence the characteristics of the sample can be measured continuously.

The above-mentioned embodiments may be combined appropriately.

B. Method of Producing a SPR Sensor Cell

The SPR sensor cell of the present invention can be produced by any suitable method. As an example, a method of producing an SPR sensor cell adopting a stamper system as a method of forming a core layer on an under-cladding layer is described. As the method of forming a core layer on an under-cladding layer, for example, photolithography (direct exposure system) using a mask as well as the stamper system may be utilized. It should be noted that photolithography is well known.

Figure 7A:
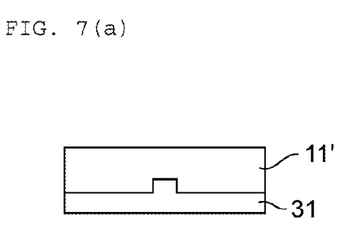
FIGS. 7(a) to 7(h) are schematic sectional views illustrating an example of a method of producing an SPR cell of the present invention.
Figure 7B:
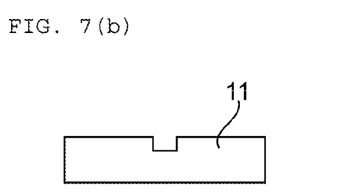

FIGS. 7(a) to 7(h) are schematic sectional views illustrating the method of producing an SPR sensor cell adopting a stamper system as a method of forming a core layer on an under-cladding layer. First, as illustrated in FIG. 7(a), a material 11' for forming an under-cladding layer is applied to a die 31 having a protrusion corresponding to a core layer formation portion of the under-cladding layer, and the material for forming an under-cladding layer applied to the die is irradiated with ultraviolet rays to cure the material. The irradiation conditions of ultraviolet rays can be set appropriately depending on the kind of the material for forming an under-cladding layer. The under-cladding layer 11 is formed by curing the material for forming an under-cladding layer. Further, as illustrated in FIG. 7(b), the under-cladding layer 11 thus formed is peeled from the die.

Figure 7C:
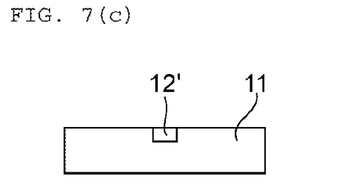
Figure 7D:
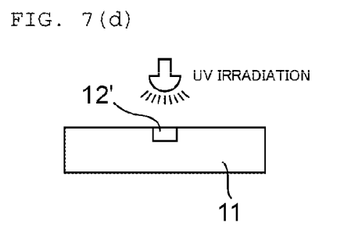
Figure 7E:
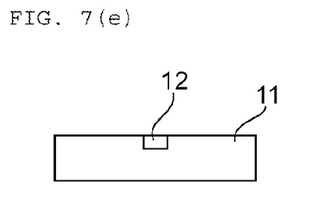

Then, as illustrated in FIG. 7(c), a groove portion of the under-cladding layer 11 is filled with a material 12' for forming a core layer. Further, of the material for forming a core layer filling the groove portion of the under-cladding layer, an excess material for forming a core layer running off the concave groove is scraped with a scraper in accordance with a method of producing a polymer optical waveguide that is described in JP 09-281351 A. Thus, the core layer and the under-cladding layer can be rendered flush with each other. Further, as illustrated in FIG. 7(d), the material 12' for forming a core layer filling the groove portion is irradiated with ultraviolet rays to be cured. The irradiation conditions of ultraviolet rays can be set appropriately depending on the kind of the material for forming a core layer. As necessary, the material for forming a core layer may be heated. The heating may be performed before or after the irradiation with ultraviolet rays, or simultaneously with the irradiation with ultraviolet rays. The heating conditions can be set appropriately depending on the kind of the material for forming a core layer. By curing the material for forming a core layer, as illustrated in FIG. 7(e), the core layer 12 buried in the under-cladding layer 11 is formed.

Figure 7F:
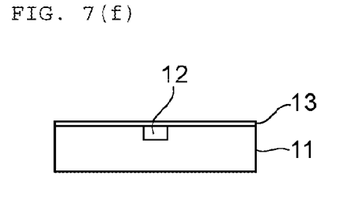

As required, as illustrated in FIG. 7(f), the protective layer 13 is formed on the under-cladding layer 11 and the core layer 12. The protective layer is formed, for example, by subjecting a material for forming a protective layer to sputtering or vapor deposition. In the case of forming the protective layer, an easy-adhesion layer (not shown) is preferably formed on the protective layer. The easy-adhesion layer is formed, for example, by subjecting chromium or titanium to sputtering.

Figure 7G:
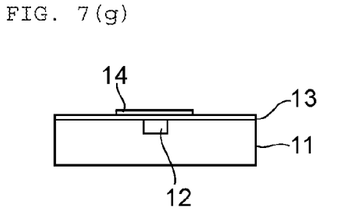

Next, as illustrated in FIG. 7(g), the metal layer 14 is formed on the protective layer 13 (upper surface of each of the core layer and the under-cladding layer in the case of not forming the protective layer) so as to cover the core layer 12. Specifically, the metal layer 14 is formed, for example, by subjecting a material for forming a metal layer to vacuum deposition, ion plating, or sputtering through a mask having a predetermined pattern.

Figure 7H:
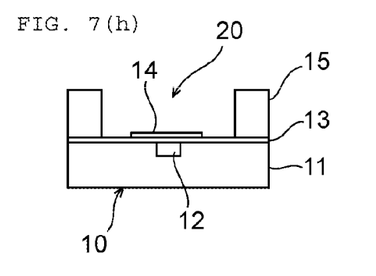

Finally, as illustrated in FIG. 7(h), the over-cladding layer 15 having the predetermined frame shape is formed. The over-cladding layer 15 can be formed by any suitable method. The over-cladding layer 15 can be formed, for example, by disposing a die having the predetermined frame shape on the protective layer 13, filling the die with varnish of a material for forming an over-cladding layer, drying the varnish, curing the varnish as necessary, and finally removing the die. In the case of using a photosensitive material, the over-cladding layer 15 can be formed by applying the varnish over the entire surface of the protective layer 13, drying the varnish, and then exposing the varnish to light through a photomask having a predetermined pattern, followed by development.

Accordingly, the SPR sensor cell can be produced by the method described above.

C. SPR Sensor

Figure 8:
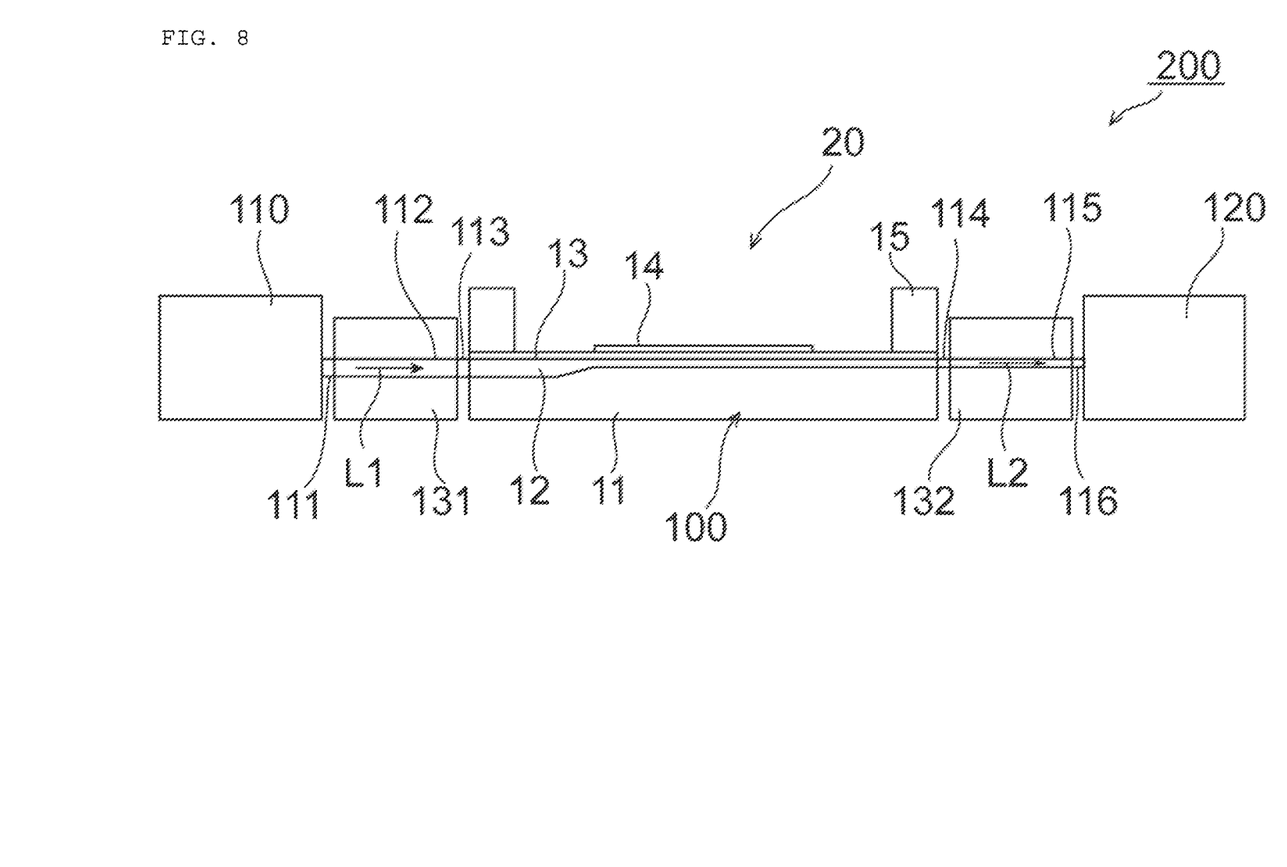
FIG. 8 is a schematic sectional view illustrating an SPR sensor according to a preferred embodiment of the present invention.

FIG. 8 is a schematic sectional view illustrating an SPR sensor according to a preferred embodiment of the present invention. An SPR sensor 200 includes the SPR sensor cell 100, a light source 110, and an optical measuring instrument 120. The SPR sensor cell 100 is the SPR sensor cell of the present invention (the SPR sensor cell as illustrated in FIG. 1) described in the above-mentioned sections A and B.

As the light source 110, any suitable light source can be adopted. Specific examples of the light source include a white light source and a monochromatic light source. The optical measuring instrument 120 is connected to any suitable arithmetic processing device, and enables accumulation, display, and processing of data.

The light source 110 is connected to a light source side optical fiber 112 through a light source side optical connector 111. The light source side optical fiber 112 is connected to one side end portion in a propagation direction of the SPR sensor cell 100 (core layer 12) through a light source side fiber block 113. A measuring instrument side optical fiber 115 is connected to the other side end portion in the propagation direction of the SPR sensor cell 100 (core layer 12) through a measuring instrument side fiber block 114. The measuring instrument side optical fiber 115 is connected to the optical measuring instrument 120 through a measuring instrument side optical connector 116.

The SPR sensor cell 100 is fixed by any suitable sensor cell fixing device (not shown). The sensor cell fixing device is movable in a predetermined direction (for example, a width direction of the SPR sensor cell), and thus the SPR sensor cell can be disposed at a desired position.

The light source side optical fiber 112 is fixed by a light source side optical fiber fixing device 131, and the measuring instrument side optical fiber 115 is fixed by a measuring instrument side optical fiber fixing device 132. The light source side optical fiber fixing device 131 and the measuring instrument side optical fiber fixing device 132 are each fixed to any suitable six-axis movable stage (not shown) so as to be movable in the propagation direction of the optical fiber, width direction (direction orthogonal to the propagation direction in a horizontal direction) and thickness direction (direction orthogonal to the propagation direction in a perpendicular direction), and rotatable about axes in the above-mentioned respective directions.

In the SPR sensor as described above, the light source 110, the light source side optical fiber 112, the SPR sensor cell 100 (core layer 12), the measuring instrument side optical fiber 115, and the optical measuring instrument 120 can be arranged on one axis, and light can be guided from the light source 110 so as to be transmitted therethrough.

An example of the manner of use of such an SPR sensor is described below.

First, a sample is mounted on the sample mounting portion 20 of the SPR sensor cell 100 so that the sample and the metal layer 13 are brought into contact with each other. Then, predetermined light from the light source 110 is guided to the SPR sensor cell 100 (core layer 12) through the light source side optical fiber 112 (see an arrow L1 of FIG. 8). The light guided to the SPR sensor cell 100 (core layer 12) is transmitted through the SPR sensor cell 100 (core layer 12) while repeating total internal reflection in the core layer 12, and part of the light enters the metal layer 13 on an upper surface of the core layer 12 and is attenuated by surface plasmon resonance. The light transmitted through the SPR sensor cell 100 (core layer 12) is guided to the optical measuring instrument 120 through the measuring instrument side optical fiber 115 (see an arrow L2 of FIG. 8). That is, in the SPR sensor 200, the intensity of light having a wavelength generating surface plasmon resonance in the core layer 12 is attenuated in the light guided to the optical measuring instrument 120. The wavelength of light generating surface plasmon resonance depends on, for example, the refractive index of the sample brought into contact with the metal layer 14. Therefore, by detecting the attenuation of the light intensity of the light guided to the optical measuring instrument 120, a change in refractive index of the sample can be detected.

For example, in the case of using a white light source as the light source 110, a change in refractive index of the sample can be confirmed by measuring the wavelength of light whose light intensity is attenuated after transmission through the SPR sensor cell 100 (wavelength of light generating surface plasmon resonance) with the optical measuring instrument 120 and detecting a change in wavelength of the light whose light intensity is attenuated. In addition, for example, in the case of using a monochromatic light source as the light source 110, a change in wavelength of light generating surface plasmon resonance can be confirmed and a change in refractive index of the sample can be confirmed by measuring a change (attenuation degree) in light intensity of monochromatic light after transmission through the SPR sensor cell 100 with the optical measuring instrument 120 and detecting a change in attenuation degree.

As described above, such an SPR sensor cell can be used, for example, for various chemical analyses and biochemical analyses such as the measurement of a sample concentration and the detection of an immunoreaction, based on a change in the refractive index of the sample. More specifically, for example, in the case where the sample is a solution, the refractive index of the sample (solution) depends on the concentration of the solution, and hence the concentration of the sample can be measured by detecting the refractive index of the sample. Further, a change in concentration of the sample can be confirmed by detecting a change in the refractive index of the sample. In addition, for example, in the detection of an immunoreaction, an antibody is fixed onto the metal layer 14 of the SPR sensor cell 100 through an intermediate dielectric film, and an analyte is brought into contact with the antibody. If the antibody and the analyte perform an immunoreaction, the refractive index of the sample changes. Therefore, it can be determined that the antibody and the analyte have performed an immunoreaction by detecting a change in refractive index of the sample before and after contact between the antibody and the analyte.

EXAMPLES

The present invention is hereinafter described specifically by way of the Examples. However, the present invention is not limited to the Examples below. It should be noted that, unless otherwise specified, a measurement wavelength for a refractive index is 850 nm and a measurement wavelength for each of an absorption coefficient and an extinction coefficient is 1,200 nm in the Examples and the Comparative Examples.

Example 1

An optical waveguide was formed through use of the stamper system as illustrated in FIGS. 7(a) to 7(e). Specifically, a fluorine-based UV curable resin ("OP38Z" (trade name) manufactured by DIC Corporation), which was a material for forming an under-cladding layer, was applied onto a die having formed thereon the shape pattern of a core layer, and was cured with ultraviolet rays to form an under-cladding layer. The refractive index of the under-cladding layer thus obtained was 1.372. The under-cladding layer had a length of 80 mm, a width of 80 mm, and a thickness of 150 µm, and a groove portion corresponding to the shape pattern of a core layer was formed in the under-cladding layer. After the under-cladding layer was peeled from the die, the groove portion was filled with a fluorine-based UV curable resin ("OP40Z" (trade name) manufactured by DIC Corporation), which was a material for forming a core layer, to form a core layer. The refractive index of the core layer thus formed was 1.399, and the absorption coefficient thereof was $2.90 \times 10^{-2}$ ($mm^{-1}$). It should be noted that the refractive index was measured by forming a film of the material for forming a core layer having a thickness of 10 µm on a silicon wafer and measuring the refractive index of the film at a wavelength of 850 nm through the use of a prism coupler refractive index measurement device. The absorption coefficient was measured by forming a film of the material for forming a core layer having a thickness of 50 µm on a glass substrate and measuring the absorption coefficient of the film at a wavelength of 1,200 nm through use of a spectrophotometer. As described above, a buried-type optical waveguide film was produced.

Then, $SiO_2$ was sputtered onto the entire surface of an upper surface (core layer exposed surface) of the optical waveguide film thus obtained to form a protective layer (thickness: 10 nm). The optical waveguide film with the protective layer formed thereon was subjected to die cutting to a length of 20 mm and a width of 20 mm. After that, chromium and gold were sequentially sputtered through a mask with an opening having a length of 2 mm and a width of 1 mm, and thus an easy-adhesion layer (thickness: 1 nm) and a metal layer (thickness: 50 nm) were sequentially formed so as to cover the core layer through the intermediation of the protective layer. Finally, an over-cladding layer having a frame shape was formed using the same material as the material for forming the under-cladding layer by a method similar to that for the formation of the under-cladding layer. Thus, an SPR sensor cell as illustrated in FIGS. 1, 2, and 3(a) to 3(c) was produced. It should be noted that, in the obtained SPR sensor cell, the sectional shape of the core layer at the light entrance was a rectangular shape having a thickness of 50 µm and a width of 50 µm, and a region ranging from the end portion of the part covered by the metal layer on the light entrance side to the light exit had a square column shape with a sectional shape having a thickness of 25 µm and a width of 25 µm.

The SPR sensor cell obtained as described above, a halogen light source ("HL-2000-HP" (trade name) manufactured by Ocean Optics, Inc.), and a spectroscope ("USB4000" (trade name) manufactured by Ocean Optics, Inc.) were arranged on one axis and connected to each other to produce an SPR sensor as illustrated in FIG. 8. 40 µL of ultrapure water were loaded into the sample mounting portion of the SPR sensor cell, white light from the light source was allowed to enter through the light entrance of the core layer via a multi-mode optical fiber having a diameter of 50 µm, and light that exited through the light exit was subjected to measurement with the spectrometer. Next, a transmittance spectrum was determined while defining, as 100%, a light intensity at each wavelength in the case where light was allowed to pass through the SPR sensor cell (optical waveguide) under a state in which ultrapure water was not mounted, and the minimum value of the transmittance was measured. Table 1 shows the result. It should be noted that a smaller minimum value means higher detection sensitivity.

Example 2

An SPR sensor cell and an SPR sensor were produced in the same way as in Example 1 except that the sectional shape of the core layer at the light entrance was a rectangular shape having a thickness of 50 μm and a width of 50 μm, and the region ranging from the end portion of the part covered by the metal layer on the light entrance side to the light exit had a square column shape with a sectional shape having a thickness of 10 μm and a width of 25 μm. The obtained SPR sensor was evaluated in the same way as in Example 1. Table 1 shows the result.

Example 3

An SPR sensor cell and an SPR sensor were produced in the same manner as in Example 1 except that the sectional shape of the core layer at the light entrance was a rectangular shape having a thickness of 50 μm and a width of 50 μm, and the region ranging from the end portion of the part covered by the metal layer on the light entrance side to the light exit had a square column shape with a sectional shape having a thickness of 10 μm and a width of 10 μm. The obtained SPR sensor was evaluated in the same way as in Example 1. Table 1 shows the result.

Example 4

An SPR sensor cell and an SPR sensor were produced in the same manner as in Example 1 except that the sectional shape of the core layer at the light entrance was a rectangular shape having a thickness of 50 μm and a width of 50 μm, and the region ranging from the end portion of the part covered by the metal layer on the light entrance side to the light exit had a square column shape with a sectional shape having a thickness of 5 μm and a width of 50 μm. The obtained SPR sensor was evaluated in the same way as in Example 1. Table 1 shows the result.

Example 5

An SPR sensor cell and an SPR sensor were produced in the same manner as in Example 1 except that the sectional shape of the core layer at the light entrance was a rectangular shape having a thickness of 100 μm and a width of 50 μm, and the region ranging from the end portion of the part covered by the metal layer on the light entrance side to the light exit had a square column shape with a sectional shape having a thickness of 25 μm and a width of 25 μm. The obtained SPR sensor was evaluated in the same way as in Example 1. Table 1 shows the result.

Example 6

An SPR sensor cell and an SPR sensor were produced in the same manner as in Example 1 except that the sectional shape of the core layer at the light entrance was a rectangular shape having a thickness of 100 μm and a width of 100 μm, and the region ranging from the end portion of the part covered by the metal layer on the light entrance side to the light exit had a square column shape with a sectional shape having a thickness of 25 μm and a width of 25 μm. The obtained SPR sensor was evaluated in the same way as in Example 1. Table 1 shows the result.

Comparative Example 1

An SPR sensor cell and an SPR sensor were produced in the same way as in Example 1 except for forming a square column-shaped core layer whose sectional shape at each of the light entrance and the light exit was a rectangular shape having a thickness of 50 μm and a width of 50 μm. The obtained SPR sensor was evaluated in the same way as in Example 1. Table 1 shows the result.

TABLE 1

| | Shape of core layer | | | | | | Minimum value of transmittance (%) |
|---|---|---|---|---|---|---|---|
| | Light entrance | | | Under metal layer | | | |
| | Thickness (μm) | Width (μm) | Sectional area S1 (μm$^2$) | Thickness (μm) | Width (μm) | Sectional area S2 (μm$^2$) | |
| Example 1 | 50 | 50 | 2,500 | 25 | 25 | 625 | 82 |
| Example 2 | 50 | 50 | 2,500 | 10 | 25 | 250 | 52 |
| Example 3 | 50 | 50 | 2,500 | 10 | 10 | 100 | 44 |
| Example 4 | 50 | 50 | 2,500 | 5 | 50 | 250 | 16 |
| Example 5 | 100 | 50 | 5,000 | 25 | 25 | 625 | 79 |
| Example 6 | 100 | 100 | 10,000 | 25 | 25 | 625 | 75 |
| Comparative Example 1 | 50 | 50 | 2,500 | 50 | 50 | 2,500 | 91 |

<Evaluation>

As is apparent from Table 1, in the case where the sectional area (S1) of the core layer at the light entrance and its sectional area (S2) at the part covered by the metal layer satisfy the relationship of S1>S2, the minimum value of the transmittance is small and the detection sensitivity is improved as compared to the case where S1=S2. In addition, such an effect can be obtained in a more suitable manner when the thickness at the part covered by the metal layer is small.

INDUSTRIAL APPLICABILITY

The SPR sensor cell and SPR sensor of the present invention can be used suitably in various chemical analyses and biochemical analyses such as the measurement of a sample concentration and the detection of an immunoreaction.

REFERENCE CHARACTERS LIST 10 detection unit
11 under-cladding layer
12 core layer
13 protective layer
14 metal layer
15 over-cladding layer
20 sample mounting portion
100 SPR sensor cell
110 light source
120 optical measuring instrument
200 SPR sensor

The invention claimed is:

1. An SPR sensor cell, comprising:
an under-cladding layer;
a core layer formed so that at least a part of the core layer is adjacent to the under-cladding layer and having a light entrance and a light exit; and
a metal layer covering a predetermined length of the core layer,
wherein a sectional area (S1) of the core layer at the light entrance and a sectional area (S2) of the core layer at the predetermined length covered by the metal layer satisfy a relationship of S1×0.5≥S2, and
a sectional shape and area of the core layer at the sectional area (S2) covered by the metal layer is constant across the predetermined length of the core layer.

2. An SPR sensor cell according to claim 1, wherein a thickness of the core layer across the sectional area (S2) covered by the metal layer is 25 μm or less.

3. An SPR sensor cell according to claim 1, wherein a thickness of the core layer at the light entrance of the sectional area (S1) is 50 μm or more.

4. An SPR sensor cell according to claim 1, wherein a width of the core layer at the light entrance of the sectional area (S1) is 50 μm or more.

5. An SPR sensor, comprising the SPR sensor cell according to claim 1.

* * * * *